United States Patent [19]
Soltys et al.

[11] Patent Number: 5,200,181
[45] Date of Patent: Apr. 6, 1993

[54] ORAL BILIRUBIN THERAPY

[75] Inventors: Paul J. Soltys, Somerville; Claudy J. P. Mullon, Burlington; Robert S. Langer, Somerville, all of Mass.

[73] Assignee: Massachusetts Institute of Technology, Cambridge, Mass.

[21] Appl. No.: 593,345

[22] Filed: Oct. 1, 1990

Related U.S. Application Data

[63] Continuation of Ser. No. 142,129, Jan. 11, 1988, abandoned.

[51] Int. Cl.$^5$ .................. A61K 37/50; A61K 37/52; A61K 9/14; C12N 11/00
[52] U.S. Cl. ................... 424/94.3; 424/94.4; 424/94.5; 424/489; 435/174; 435/177; 435/178; 435/179
[58] Field of Search .............. 424/94.3, 94.4, 94.5, 424/489; 435/174, 177, 178, 179

[56] References Cited

U.S. PATENT DOCUMENTS

| | | | |
|---|---|---|---|
| 992,254 | 5/1911 | Rieck | 424/94.3 |
| 4,363,801 | 12/1982 | Nagyvary | 514/893 |
| 4,701,411 | 10/1987 | Wu | 424/94.4 |

OTHER PUBLICATIONS

Bourget et al., Biochimica et Biophysica Acta, 883 (1986) pp. 432-438.
Gardner et al., in Biomedical Applications of Immobilized Enzymes and Proteins, Chang, ed., vol. 1, ©1977, Plenun Press, N.Y., pp. 163-170.
McDonagh et al., Science 208:145-151 (1980).
McDonagh et al., J. Clin. Invest. 66:1182-1185 (1980).
Freston et al., Kidney Intern. 10:S-229 (1976).
Sideman et al., Am. Soc. Art. Intern. Org. J., 4, 164 (1981).
Lavin et al., Science 230:(4725):543 (1985).
Odell et al., Ped. Res., 17, 810 (1983).
Poland and Odell, Proc. Soc. Exp. Biol. Med. 146:1114 (1974).

*Primary Examiner*—Jacqueline Stone

[57] ABSTRACT

Levels of bilirubin in mammalian serum are controlled by administering to the mammalian intestinal tract a substance (a "bilirubin deactivator") that converts unconjugated bilirubin into nontoxic, physiologically compatible products, thereby reducing reabsorption of unconjugated bilirubin in enterohepatic circulation. Useful bilirubin deactivators include those which specifically adsorb the bilirubin and are excreted, and "bilirubin conversion enzymes", i.e., enzymes that operate on the unconjugated bilirubin substrate to yield products that are physiologically compatible in that they are not reabsorbed, or, if reabsorbed, they are nontoxic in the blood stream.

4 Claims, 1 Drawing Sheet

ORAL BILIRUBIN THERAPY

This is a continuation of a co-pending application Ser. No. 07/142,129 filed on Jan. 11, 1988, now abandoned.

BACKGROUND OF THE INVENTION

This invention relates to the general field of controlling excessive levels of bilirubin.

In the human body, bilirubin is produced by the breakdown of cyclic tetrapyrroles, particularly hemoglobin. Excessive bilirubin concentrations, manifest as jaundice, can cause irreversible damage to the central nervous system.

Ordinarily, bilirubin concentration is controlled as bilirubin is filtered from the blood by the liver, where it is conjugated with glucuronic acid. The bilirubin glucuronic acid conjugate (referred to hereafter as "conjugated bilirubin") is excreted to the small intestine via the common bile duct. Bacterial flora reduce conjugated bilirubin, which is then excreted in the stool.

Excessive bilirubin is common in infants for a number of reasons including a high rate of hemolysis, immaturity of liver function necessary to form conjugated bilirubin, obstruction of the bilary system, and the absence of intestinal flora to reduce bilirubin conjugate. In the absence of intestinal flora and their reducing enzymes, conjugated bilirubin may be deconjugated, and the resulting unconjugated bilirubin may be reabsorbed by the intestine, increasing serum bilirubin concentrations.

Various therapies for excessive bilirubin are known. The two most common treatments for neonatal jaundice are phototherapy and exchange transfusion.

In phototherapy, bilirubin is converted to more readily excreted photoisomers by exposing the infant to blue light. See, e.g., McDonagh et al., *Science* 208:145-151 (1980); and McDonagh et al., *J. Clin. Invest.*, 66: 1182-1185 (1980). Phototherapy is relatively slow, and long term conseguences of blue light exposure are not known.

For severe cases of jaundice (plasma bilirubin >15 mg/dl), it may be necessary for the infant to undergo exchange transfusion. Exchange transfusion involves the replacemnmt of the infant's blood with bilirubin-free adult blocd. This procedure presents potentially fatal risks, including blood damage, fluid shifts, and risk of transmission of infectious diseases.

Other potential treatments in development stages include extracorporeal devices, such as hemoperfusion, which utilize resins to adsorb bilirubin. In hemoperfusion, the blood or plasma of a patient is passed through an affinity column. The column, which usually consists of a bed of small particles, binds bilirubin which is in the blood; the cleansed blood or plasma is then returned to the patient. For instance, Freston et al., *Kidney Intern.* 10: S-229 (1976), and Sideman et al., *Am. Soc. Art. Intern. Org. J.*, 4, 164 (1981), report removal of bilirubin from artificial plasma by hemoperfusion with uncoated and cellulose-coated carbon as well as with serum albumin coated beads. Lavin et al., *Science:*230 (4725): 543 (1985) describe an extracorporeal column containing immobilized bilirubin oxidase to reduce serum bilirubin concentration. Bilirubin oxidase catalyzes the degradation of bilirubin to biliverdin and biliverdin to other non-toxic products.

Odell et al., *Ped. Res.*, 17, 810 (1983), describe the use of agar as a nonspecific bilirubin adsorbent. Enteral administration of agar was shown to increase the efficacy of phototherapy in the treatment of neonatal hyperbilirubinemia. The binding capacity of agar for bilirubin was positively correlated to the sulfate and to the calcium content of the agar as described by Poland and Odell, *Proc. Soc. Exp. Biol. Med.*, 146: 1114 (1974).

SUMMARY OF THE INVENTION

We have discovered that levels of bilirubin in mammalian serum can be controlled by administering to the mammalian intestinal tract a substance (a "bilirubin deactivator") that converts unconjugated bilirubin into nontoxic, physiologically compatible products, thereby reducing reabsorption of unconjugated bilirubin in enterohepatic circulation. Bilirubin deactivators useful in the invention include those which specifically adsorb bilirubin and are excreted (i.e., they undergo surface physical interaction with bilirubin, thereby physically removing it from liquid-phase reactions). Other useful bilirubin deactivators are "bilirubin conversion enzymes", i.e., enzymes that operate on the unconjugated bilirubin substrate to yield products that are physiologically compatible in that they are not reabsorbed, or, if reabsorbed, they are nontoxic in the blood stream.

The bilirubin deactivator is preferably introduced in the intestinal tract or lumen (specifically the area adjacent the bile duct) by oral administration in a stabilized form. For example, the deactivator is carried by an inert carrier such as a solid support resistant to intestinal degradation. The method is particularly effective for mammals (e.g., human neonates) lacking intestinal flora for converting conjugated bilirubin to excretion products.

The method is simple and noninvasive, requiring only the oral ingestion of, e.g., microbeads. The method can be combined with other methods, such as phototherapy, and may increase the effectiveness of such treatments, particularly treatments such as phototherapy whose effectiveness is undercut by enhanced biliary secretion of unconjugated bilirubin.

Other features and advantages of the invention will be apparent from the following description of a preferred embodiment thereof and from the claims.

DESCRIPTION OF THE PREFERRED EMBODIMENT

Figure 1:
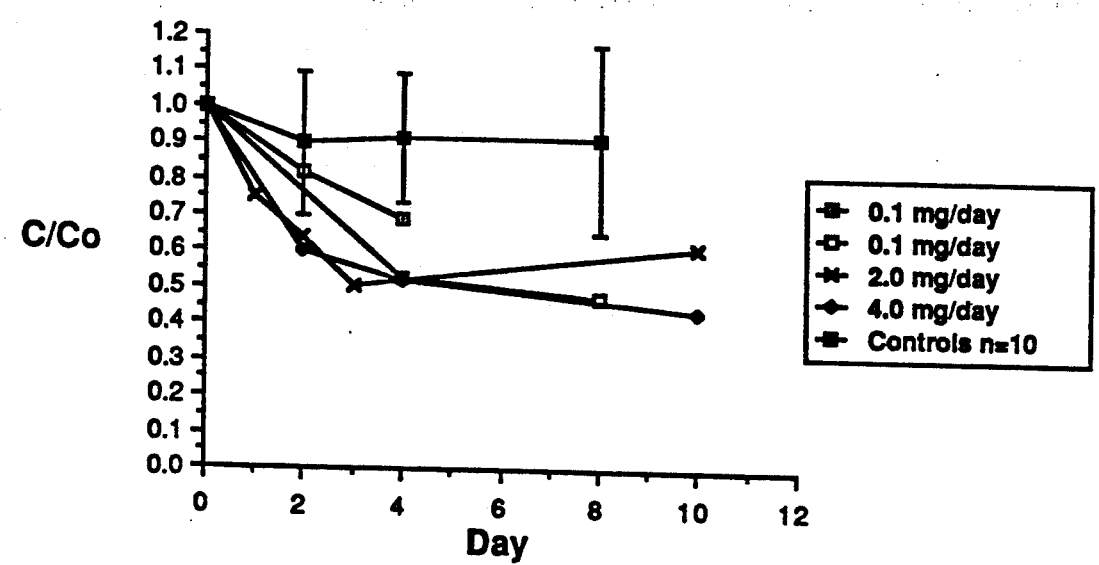

We first briefly describe the Figure.

Drawing

FIG. 1 is a graph depicting the results of experiments described below.

CONVERSION ENZYMES

The preferred bilirubin conversion enzymes are those which tolerate the intestinal environment, and which convert unconjugated bilirubin to relatively harmless products. For example, bilirubin oxidase catalyzes the oxidation of bilirubin with $O_2$, initially producing biliverdin, which then may be oxidized further. Such bilirubin oxidation products apparently are not teratogenic, cytotoxic, or mutagenic. See Levin et al., cited above.

Bilirubin oxidase is obtained from *Myrothecium verricaria* and can be purified from this organism as described by Murao et al., *Agric. Biol. Chem.*, 46:2031 (1982) and Tanaka et al., *Agric. Biol. Chem.* 46:2499 (1982). See also, Broderson et al. *Eur. J. Biochem.* 10:468 (1969). and Eiichi et al., French 2,576,909 and JP appl'n. 85/20625.

Bilirubin Adsorbents

Suitable bilirubin-specific adsorbents include activated carbon, cellulose that has been coated with serum albumin or Y-protein (ligandin), which is known to be useful to study bilirubin uptake in hepatocytes. Stollman et al. *J. Clin. Invest.* 72:718 (1983). Albumin-coated cellulose is described in the following references: Sideman et al., *Proc. Int'l. Sympos. on Art. Liver Support,* 103 (1981); Sideman et al., *Am. Soc. Art. Intern. Org. J.* 4:164 (1981); Plotz et al., *J. Clin. Invest.* 53:778 (1974); Scharschmidt et al., *J. Clin. Invest.* 53:786 (1974); and Scharschmidt et al., *Lab. & Clin. Med.* 89:101 (1977). Y-protein can be obtained as described by Litwack et al. *Nature* 234:466 (1977), or Arlas, *J. Clin. Invest.* 51:677 (1972).

The inert carrier is preferably a polymeric bead that is stable to passage through the mammalian intestinal tract and physiologically inert. The beads should be small enough for easy oral administration to neonates. The carrier also preferably enhances the enzyme's resistance to functional denaturation over that of its soluble form, and reduces losses of activity from denaturing conditions in the stomach and intestine. Suitable beads include agarose beads, for example, Sepharose 4B CL beads (Pharmacia), which mammals cannot degrade.

The bilirubin conversion enzyme can be immobilized on the carrier by various known techniques, e.g., the cyanogen bromide and tresyl chloride activation procedure described by Kohn et al., *Biochem. Biophys. Res. Com.* 107:878 (1982) and Nilsson and Mosbach, *Biochem. Biophys. Res. Com.* 102:449 (1981), respectively.

The following specific example is provided to illustrate the invention, and does not limit its scope.

EXAMPLE

Bilirubin oxidase, purchased from Kodak Bio-Products, was immobilized on tresyl chloride activated agarose beads as cited above. Bilirubin oxidase activity was measured, in vitro, using a human serum albumin-bilirubin mixture with a molar ratio of 0.7. Under conditions encountered in the stomach (37° C., pH 3.0, for one hour), the enzymatic activity was substantially retained (90% retention).

Bilirubin oxidase immobilized to agarose, prepared as described above, was administered orally to Gunn rats (350 g) (Blue Spruce Vendors) as follows. Each day, the rats received 15 grams of regular chow (Whitmer et al., *Semin. Liver Dis.* 3:42 (1983)). Enzyme-agarose conjugate in a freeze-dried form was mixed thoroughly with the chow for three days. After day three, the rats were fed the same amount of chow without the enzyme-agarose supplement. Control rats were fed each day with either 15 grams of chow or 15 grams of chow and agarose without the enzyme agarose conjugate. Plasma bilirubin concentrations (C) were measured daily using the assay described by Jendrassik and Grof, *Biochem. Z.* 297:81 (1938) and were normalized with respect to the initial plasma bilirubin concentrations (Co) from day 0. By day 3, test rats receiving enzyme had C/Co values close to 0.5. When enzyme administration was discontinued, plasma bilirubin levels in test rats were slow to recover to original levels. Control rats experienced steady plasma bilirubin levels after an initial decrease as shown by FIG. 1.

The above experiment was performed three additional times, under substantially identical conditions, except for dosage. In one of those experiments, the test dosage was 2.0 mg. bilirubin immobilized to 0.2 g agarose; the control agarose dosage was 0.2 g. In the next experiment, the test dosage was 4.0 mg. bilirubin immobilized to 0.4 g agarose; and the control agarose dosage was 0.4 g. In the final experiment, the test dosage was 0.1 mg enzyme immobilized to 10 mg dry agarose. The results are shown in FIG. 1.

In an additional control, enzyme immobilized to agarose was heat denatured (incubated at 45° C. for 68 hours) prior to its addition to the feed chow. After denaturation, in vitro assays revealed no enzymatic activity of the enzyme-agarose conjugate. Values of C/Co for the test animals were 0.53 and 0.69; for six control animals the values averaged 0.93.

OTHER EMBODIMENTS

Other enzymes and carriers can be used in the invention, as well as other modes of intestinal administration.

Nonenzymatic bilirubin deactivators can be used, e.g., bilirubin specific adsorbents that are excreted and thereby remove unconjugated bilirubin from the intestinal tract. Suitable adsorbents include: activated carbon, agarose, and cellulose supports coated with serum albumin or Y protein (ligandin). Serum albumin and Y-protein serve as natural carriers by binding bilirubin in the bloodstream and in the liver, respectively.

We claim:

1. A method of controlling serum bilirubin levels in a mammal by administering a bilirubin conversion enzyme via the stomach to the mammal's intestinal tract, said enzyme being conjugated to an inert polymeric particulate carrier resistant to intestinal degradation.

2. The method of claim 1 wherein said bilirubin conversion enzyme is bilirubin oxidase or UDP glucuronyl transferase.

3. The method of either claim 1 or claim 2 wherein said bilirubin conversion enzyme, conjugated to an inert carrier, is administered orally.

4. The method of claim 1 wherein said inert polymeric particulate carrier comprises resinous beads.

* * * * *